US006895282B2

(12) United States Patent
Gellman et al.

(10) Patent No.: US 6,895,282 B2
(45) Date of Patent: May 17, 2005

(54) INDUCTION HEATING FOR THE DELIVERY OF THERMAL THERAPY

(75) Inventors: Barry N. Gellman, N. Easton, MA (US); Jozef Slanda, Milford, MA (US); Kimberly Paddock, Newton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 97 days.

(21) Appl. No.: 10/264,969

(22) Filed: Oct. 4, 2002

(65) Prior Publication Data

US 2004/0068308 A1 Apr. 8, 2004

(51) Int. Cl.⁷ .......................... A61F 2/00; A61M 37/00

(52) U.S. Cl. ........................................ 607/103; 600/12

(58) Field of Search ........................ 600/10–13; 607/96, 607/103; 128/899

(56) References Cited

U.S. PATENT DOCUMENTS

| | | | | |
|---|---|---|---|---|
| 4,186,729 A | 2/1980 | Harrison | ..................... | 128/1.3 |
| 4,237,898 A | 12/1980 | Whalley | ..................... | 128/422 |
| 4,269,199 A | 5/1981 | Armitage | ..................... | 128/804 |
| 4,454,883 A | 6/1984 | Fellus | ..................... | 128/422 |
| 4,702,262 A | 10/1987 | Andersen et al. | ............ | 128/804 |
| 4,951,688 A | 8/1990 | Keren | ..................... | 128/804 |

(Continued)

FOREIGN PATENT DOCUMENTS

| | | | | |
|---|---|---|---|---|
| EP | 0 713 715 | 11/1994 | | |
| EP | 0 888 748 | 6/1997 | | |
| JP | 2002136537 | 5/2002 | ............. | A61F/7/12 |
| WO | 98/34564 | 8/1998 | ............. | A61F/2/06 |
| WO | WO 98/38932 | 11/1998 | | |
| WO | 99/55398 | 11/1999 | | |

OTHER PUBLICATIONS

Akagi et al., "Anti–tumor effects of localized hyperthermia on a experimental bone tumor u sing an interamedullary nail," *Int. J. Hyperthermia*, vol. 13, No. 4, pp. 387–400, (1997).

Jorgensen et al., "Electrochemical Therapy of Pelvic Pain: Effects of Pulsed Electromagnetic Fields (PEMF) on Tissue Trauma," *Eur J Surg*, Suppl 574: pp. 83–86, (1994).

Kobayashi et al., "Interstitial hyperthermia of experimental brain tumor using implant heating system," *Journal of Neuro–Oncology*, vol. 7, pp. 201–208, (1989).

Oleson et al., "Hyperthermia by Magnetic Induction: Experimental and Theoretical Results for Coaxial Coil Pairs," *Radiation Research*, vol. 95, pp. 175–186, (1983).

Oleson et al., "Hyperthermia by Magnetic Induction: II. Clinical Experience with Concentration Electrodes," *Int. J. Radiation Oncology Biol. Phys.*, vol. 9, pp. 549–556, (1982).

Oleson et al., "Regional Hyperthermia by Magnetic Induction in a Beagle Dog Model: Analysis of Thermal Dosimetry," *Radiation Research*, vol. 98, pp. 445–455, (1984).

(Continued)

*Primary Examiner*—Roy D. Gibson
(74) *Attorney, Agent, or Firm*—Edwards & Angell, LLP; Robert J. Tosti; Lisa Swiszcz Hazzard

(57) ABSTRACT

An induction heating apparatus includes a first interventional device and a second interventional device. The first interventional device includes an electrically conductive material. The first interventional device is adapted for implantation inside a body and for receiving an alternating current. The second interventional device comprises a magnetically conductive material. The second interventional device is adapted for implantation inside the body in close proximity to the first interventional device. With both devices placed inside the body, the second interventional device magnetically couples with the first interventional device and the second interventional device generates heat upon the application of the alternating current to the first interventional device thereby heating the body site.

30 Claims, 10 Drawing Sheets

U.S. PATENT DOCUMENTS

| | | | |
|---|---|---|---|
| 4,993,413 A | | 2/1991 | McLeod et al. ............ 128/419 |
| 4,996,481 A | | 2/1991 | Ackerman et al. .......... 324/318 |
| 5,010,897 A | | 4/1991 | Leveen ...................... 128/804 |
| 5,019,076 A | | 5/1991 | Yamanashi et al. ........... 606/45 |
| 5,197,940 A | | 3/1993 | Sievert et al. ................. 600/9 |
| 5,369,251 A | | 11/1994 | King et al. ................. 219/695 |
| 5,425,731 A | | 6/1995 | Daniel et al. ................. 606/28 |
| 5,429,582 A | | 7/1995 | Williams ....................... 600/2 |
| 5,630,426 A | | 5/1997 | Eggers et al. ............... 128/734 |
| 5,643,322 A | | 7/1997 | Ito et al. ........................ 607/2 |
| 5,690,109 A | | 11/1997 | Govind et al. ........... 128/653.2 |
| 5,827,322 A | * | 10/1998 | Williams ................... 623/1.18 |
| 5,849,020 A | | 12/1998 | Long et al. ................. 606/167 |
| 6,167,313 A | * | 12/2000 | Gray et al. ................. 607/103 |
| 6,238,421 B1 | | 5/2001 | Günther et al. ............... 607/13 |
| 6,270,472 B1 | | 8/2001 | Antaki et al. ................. 604/61 |
| 6,423,056 B1 | * | 7/2002 | Ishikawa et al. ............. 606/28 |
| 6,626,940 B2 | * | 9/2003 | Crowley .................... 623/1.42 |

OTHER PUBLICATIONS

Paulsen et al., "Theoretical Temperature Profiles for Concentric Coil Induction Heating Devices in a Two–Dimensional Axi–Asymmetric Inhomogeneous Patient Model," *Int. J. Radiation Oncology Biol. Phys.*, vol. 10, pp. 1095–1107 (1984).

Strohbehn, "Theoretical temperature distributions for solenoidal–type hyperthermia systems," *Med. Phys.* 9(5), pp. 673–682(Sep./Oct. 1982).

Tohnai et al., "Preoperative thermochemotherapy of oral cancer using magnetic induction hyperthermia (Implant Heating System: IHS)," *Int. J. Hyperthermia*, vol. 12, No. 1, pp. 37–47 (1996).

Yamanashi et al., "Precision Surgery with an Electromagnetically Induced Current Convergence Probe Application in Aneurysm Treatment, Angioplasty, and Brain Tumor Resection in in Vivo and in Vitro Models," *Association for the Advancement of Medical Instrumentation*, vol. 22, No. 4, pp. 205–216, (1988).

* cited by examiner

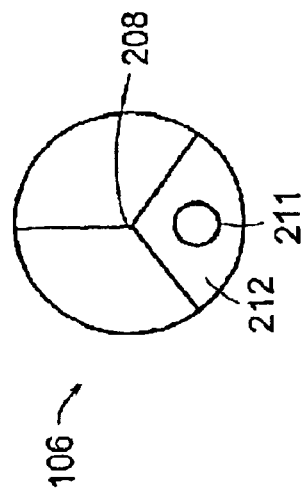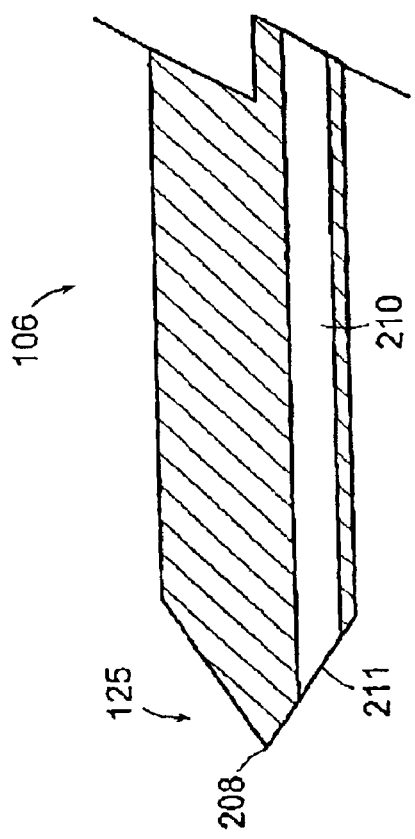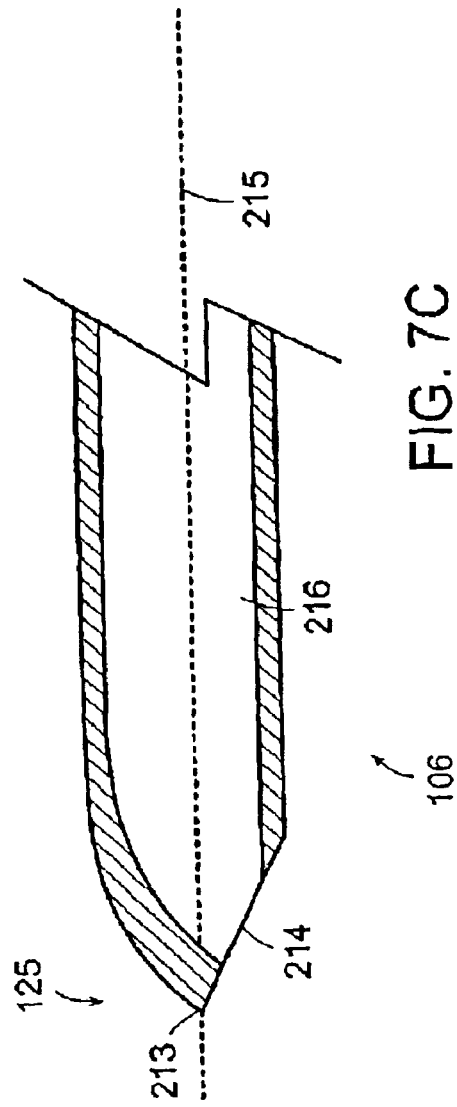
FIG. 7B
FIG. 7A
FIG. 7C

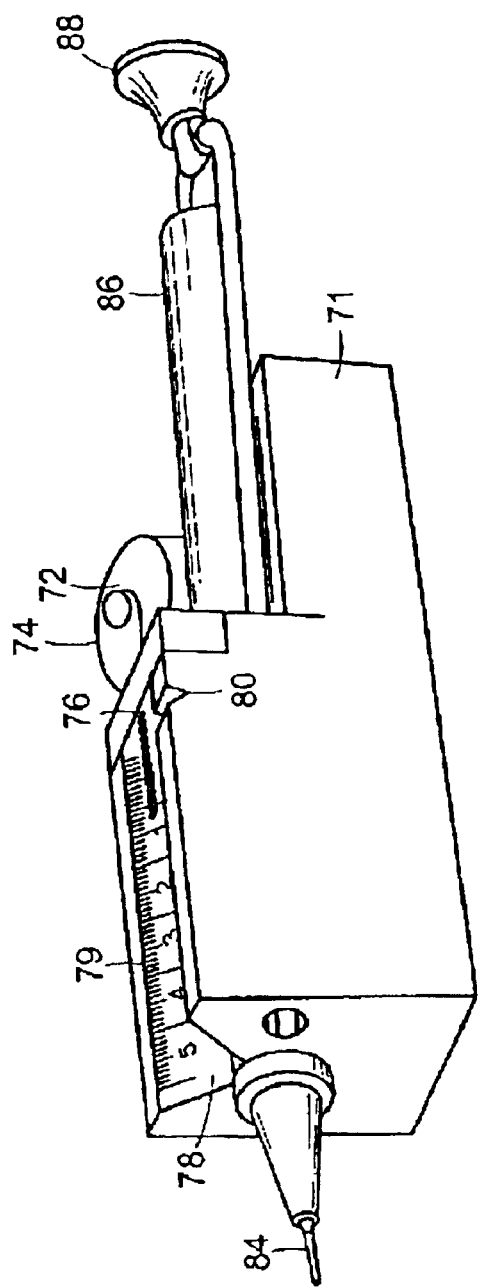
FIG. 8
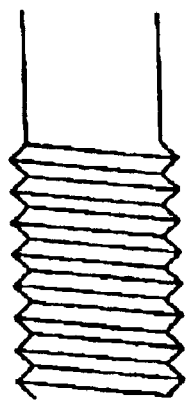
FIG. 9D
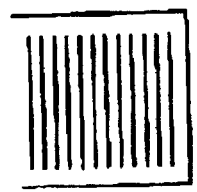
FIG. 9C
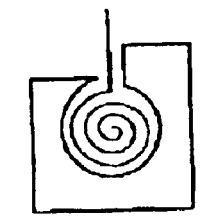
FIG. 9B
FIG. 9A

INDUCTION HEATING FOR THE DELIVERY OF THERMAL THERAPY

TECHNICAL FIELD

This invention relates to an apparatus and a method for treating tissue and, more particularly, to an apparatus and a method for treating tissue through induction heating.

BACKGROUND INFORMATION

There are many medical procedures in which tissue is treated or removed. For example, thermal therapy involving application of light or heat can be used for ablating or resecting tissue. Current thermal therapy procedures include microwave therapy, radio-frequency (RF) ablation, resection, and induction heating.

Microwave therapy involves the application of energy in the microwave frequency region to tissue to ablate the tissue. Devices for performing microwave therapy typically include a probe having a microwave antenna and a coaxial transmission line. Microwave therapy usually is performed as an outpatient procedure in a physician's office. One constraint of microwave therapy, however, is its poor ability to control the shape of the treated region by the physician. For example, when treating the prostate, the probe is positioned inside the urethra and the heat generated by the microwave energy pushes through the prostate while the urethra is being cooled. The amount of heat applied to the tissue, however, depends on the vascularity and density of the prostate tissue, thus making it difficult to control the size and shape of the treatment site.

RF ablation entails an electrode, connected to a power source, supplying radio frequency energy to tissue to ablate the tissue. RF ablation has been used conventionally for treating benign prostate hyperplasia (BPH), as well as for removing tumors. Typically, RF ablation requires surgical intervention and a multi-day hospital stay for the patient due to post-operative bleeding or retention.

Tissue resection also requires an electrode connected to a power source. The power source supplies alternating current to the electrode. The geometry of the electrode, (e.g., loop or wedge) allows a tissue chip to be carved as the electrode moves across a surface of the tissue. Tissue resection has been used conventionally in performing transurethral resection of the prostate.

Laser ablation involves application of a laser beam to vaporize tissue. This procedure can be very painful post-operatively as the procedure can sear nerve endings and cause charring of the tissue surface. When the tissue surface is charred, a greater amount of laser energy is necessary for deeper penetration into the tissue. Laser ablation thus has fallen out of favor with most physicians.

Induction heating typically involves implanting seeds inside a patient and exposing the patient to an oscillating magnetic field to cause the seeds to generate heat. The seeds are implanted inside a patient through surgery in advance. Treatment is subsequently performed in a physician's office by externally activating the seeds as the patient sits in an inductor chair that raises the temperature of the seeds through electromagnetic induction.

Conventionally, to implant the seeds, a medical operator places multiple seeds into a three-dimensional array with a needle using a two-dimensional grid pattern, and longitudinal spacing. A needle guide, called a template, typically defines the two-dimensional grid. The template includes a matrix of holes, which guide the longitudinal advancement of the needles to insure their proper two-dimensional positioning in the tissue. Subsequent to establishing the two-dimensional array of needles in the tissue, the medical operator deposits the seeds along the longitudinal axis of each needle. Biocompatible spacers typically space the seeds along the longitudinal axis of the needle. The medical operator alternately inserts spacers and seeds into the needle prior to placing the needle into the tissue. To maintain the position of the line of seeds and spacers as the needle is withdrawn, the medical operator typically employs a mandrel. This leaves a line of seeds in their proper longitudinal position. The medical operator then repeats this process at the other two-dimensional grid coordinates forming the desired three-dimensional array of seeds.

To provide effective heating over an elongated or wide target area, the seeds are typically uniformly and relatively closely spaced. The need to ensure accurate and precise implantation of numerous individual heating sources undesirably prolongs the procedure. Moreover, the use of discrete seeds requires an elaborate grid matrix for their proper implantation. This requirement is labor-intensive and costly. In addition, the discrete nature of the seeds renders them more susceptible to migration from their intended locations, thereby potentially subjecting the treatment site, and surrounding healthy tissue to over- or under-heating, reducing the effectiveness and reliability of the therapy.

In an attempt to accomplish a more even distribution of seeds in a longitudinal direction, the so-called "rapid strand" approach provides a bioabsorbable strand or suture onto which several seeds have been pre-assembled in a uniform spacing approximately 10 mm apart. Unfortunately, although spacing the seeds along the strand can generally provide a somewhat more uniform longitudinal dosage to the patient, the strand itself may not be sufficiently rigid to allow for it to be properly and reliably installed at the treatment site without becoming jammed in the delivery needles. Further, medical operators typically use 18-gauge bevel-tip needles to place seeds. Due to the bevel tip and flexibility of the hypodermic tubing of the 18-gauge needle, such needles tend to splay making it necessary for the medical operator to make multiple sticks to place the needle in the desired location.

SUMMARY OF THE INVENTION

The invention relates to systems and methods for performing thermal therapy less invasively than known systems and methods. According to one embodiment, a tissue site is treated through induction heating by placing both an inductor and a magnetically conductive heating element inside a body.

In one aspect, the invention features an induction heating apparatus. The apparatus includes a first interventional device and a second interventional device. The first interventional device includes an electrically conductive material. The first interventional device is adapted for implantation inside a body and for receiving an alternating current. The second interventional device includes a magnetically conductive material. The second interventional device is adapted for implantation inside the body in close proximity to the first interventional device. With both devices placed inside the body, the second interventional device magnetically couples with the first interventional device and generates heat upon the application of the alternating current to the first interventional device.

In some embodiments, the first interventional device includes an inductor, such as a radio-frequency coil. In one embodiment, the first interventional device further includes a carrier, such as, for example, a catheter, a stent, a probe, a guide wire, an endoscope, a needle, or a sensor. In one example, the first interventional device includes a catheter and an inductor placed in the catheter. In another example, the first interventional device includes a probe and a radio-frequency coil placed in the probe.

According to various embodiments of the invention, the second interventional device employs one of a substantially straight round wire, a substantially straight flat wire, a detented wire, an embossed wire, a bristled wire, a shaped resilient wire, a twisted round wire, a twisted flatwire, or a coil with an inner core. In one embodiment, the second interventional device includes a coil of variable length, for example, a magnet coil. In a further embodiment, the second interventional device is implantable inside the body.

In some embodiments, the induction heating apparatus also includes a power source in electrical communication with the first interventional device. In one embodiment, the power source supplies alternating current to the first interventional device. In a further embodiment, the induction heating apparatus further includes a controller in electrical communication with the power source for controlling, for example, the amplitude, frequency, and/or duration of alternating current applied to the first interventional device.

According to one aspect of this embodiment of the invention, the induction heating apparatus further includes the multi-cannula delivery system for implantation of the second interventional device inside the body. The multi-cannula delivery system includes an outer cannula and an inner cannula having a distal tip and an outer diameter sufficiently small to fit inside the outer cannula. In one embodiment of the invention, the inner cannula has an inner diameter sufficiently large to receive the second interventional device therein. According to a further embodiment, the multi-cannula delivery system further includes an outer stylet having a distal tip and an outer diameter sufficiently small to fit inside the outer cannula. According to an additional embodiment, the multi-cannula delivery system also includes an inner stylet having a distal tip and an outer diameter sufficiently small to fit inside the inner cannula.

In one embodiment of the invention, the outer cannula has an echogenic tip. In some embodiments, the inner cannula may be preloaded with the second interventional device. According to one feature of the invention, the distal tip of the inner cannula is plugged. According to another feature, the distal tip of the inner stylet has a blunt flat tip.

In one embodiment of the invention, the outer cannula and the inner cannula have longitudinal openings. According to one feature, the inner cannula is capable of rotating in relation to the outer cannula so as to cause these longitudinal openings to align. According to a further feature, the second interventional device is releasable from the multi-cannula delivery system upon alignment of these longitudinal openings.

In one embodiment of the invention, the distal tip of the inner cannula includes a Huber point. In an alternative embodiment, the distal tip of the inner cannula includes a trocar. According to one version of this embodiment, the inner cannula has an eccentric opening at the distal tip. According to alternative version of this embodiment, the inner cannula has a side opening proximal to the distal tip.

In some embodiments of the invention, the induction heating apparatus further includes a multi-cannula delivery system loading device, which includes a base, a container attached to the base and adapted for dispensing the second interventional device therefrom, and a discharge tube attached to the base and adapted for receiving the second interventional device dispensed from the container and for loading the second interventional device into the multi-cannula delivery system. In one embodiment, the base defines a groove longitudinally formed therein. According to one feature, the second interventional device is dispensed from the container into the groove. In a further embodiment, the discharge tube is disposed in the groove. Optionally, the discharge tube has a drop-in slot for receiving the second interventional device therein.

According to another feature, the discharge tube also includes an actuator and a luer port for loading the second interventional device into the multi-cannula delivery system. Optionally, the base may be adapted to facilitate cutting the second interventional device within the groove. The base may also include a cutoff scale. According to another feature of the invention, the container is replaceable with other containers of various configurations.

In general, in another aspect, the invention features a method of treating tissue. According to this aspect of the invention, a first interventional device including an electrically conductive material is inserted inside a body, and a second interventional device including a magnetically conductive material is implanted inside the body in close proximity to the first interventional device and adjacent a tissue site to be treated. An alternating current is applied to the first interventional device to generate an electromagnetic field and to induce a current in the second interventional device to heat the tissue site.

In one embodiment, an alternating current is applied to the first interventional device to induce the current in the second interventional device to treat a tumor. In another embodiment, an alternating current is applied to the first interventional device to induce the current in the second interventional device to ablate the tissue site. In one version of this embodiment, the first interventional device is inserted inside a urethra of the body and the second interventional device is inserted inside a prostate of the body to ablate a prostate tissue site. According to one feature, the second interventional device is implanted inside the prostate about one centimeter from the urethra. According to another feature, the second interventional device is implanted inside the prostate to be substantially parallel to the first interventional device inserted inside the urethra.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1A depicts an induction heating apparatus, including an inductor placed inside a carrier and a heating element, according to an illustrative embodiment of the invention;

FIG. 7A shows a cross-sectional view taken along a longitudinal axis of an inner cannula of the multi-cannula delivery system of FIG. 4A having a trocar at its distal end according to an illustrative embodiment of the invention;

FIG. 7B shows a front end view of the inner cannula of FIG. 7A;

FIG. 7C shows a cross-sectional side view taken along a longitudinal axis of an inner cannula of the multi-cannula delivery system of FIG. 4A having a Huber point at its distal end, according to another illustrative embodiment of the invention;

FIG. 8 shows a multi-cannula delivery system loading device according to an illustrative embodiment of the invention;

FIG. 9A shows a cassette adapted for handling a heating element of the induction heating apparatus of FIG. 1A, which may be employed with the multi-cannula delivery system loading device of FIG. 8, according to an illustrative embodiment of the invention;

FIG. 9B shows a cassette adapted for handling a heating element of the induction heating apparatus of FIG. 1A, which may be employed with the multi-cannula delivery system loading device of FIG. 8, according to another illustrative embodiment of the invention;

FIG. 9C shows a cassette adapted for handling a heating element of the induction heating apparatus of FIG. 1A, which may be employed with the multi-cannula delivery system loading device of FIG. 8, according to a further illustrative embodiment of the invention;

FIG. 9D shows a cassette adapted for handling a heating element of the induction heating apparatus of FIG. 1A, which may be employed with the multi-cannula delivery system loading device of FIG. 8, according to an additional illustrative embodiment of the present invention.

ILLUSTRATIVE DESCRIPTION

Figure 1B:
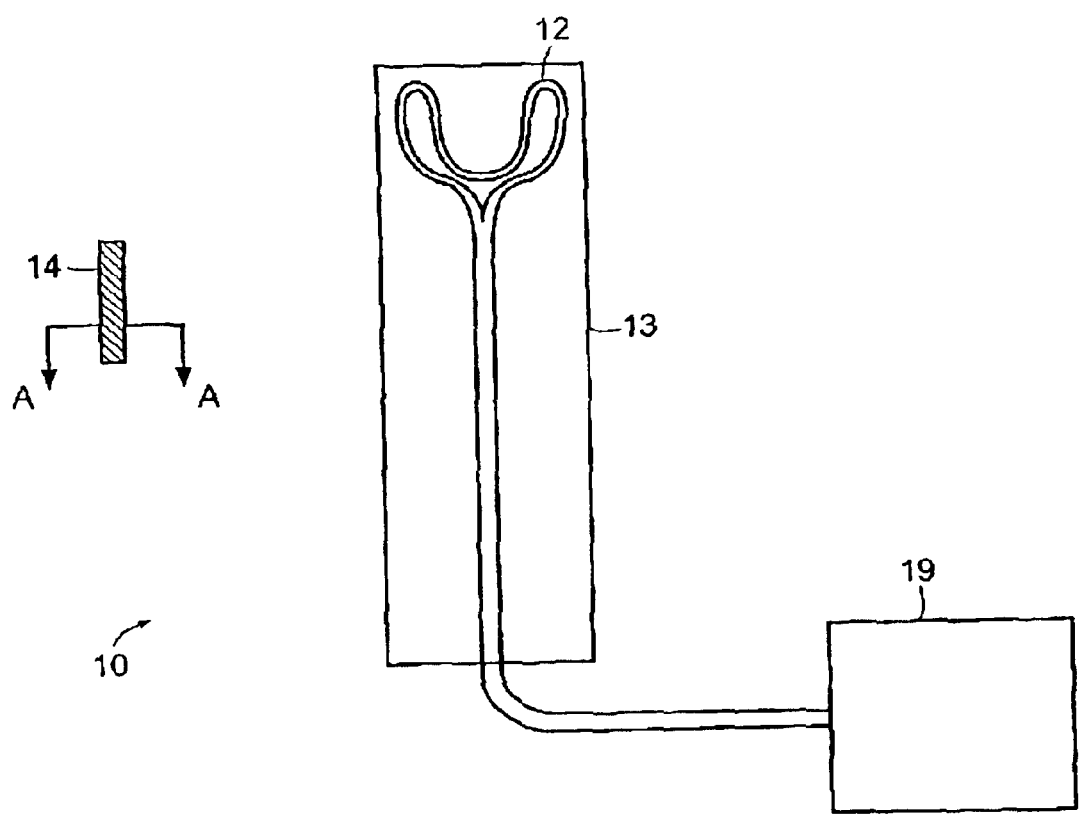
FIGS. 1B–1C show cross-sectional views, taken along the line AA, of two exemplary embodiments of the heating element, which may be employed with the induction heating apparatus of FIG. 1A.
Figure 1B:
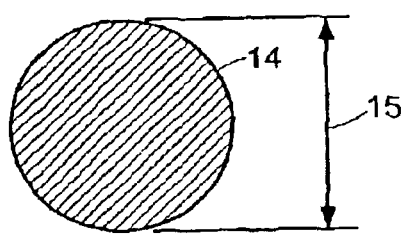

Referring to FIG. 1A, an illustrative induction heating apparatus 10 includes an inductor 12 and a heating element 14. The inductor 12 is in electrical communication with a power source, for example, a RF energy source 19. The inductor 12 includes an electrically conductive material. In one illustrative embodiment, the inductor 12 is formed as a loop. However, according to the invention, the inductor 12 may be formed in a variety of shapes suitable for generating an electromagnetic field, without deviating from the scope of the invention.

The heating element 14 includes a magnetically conductive material. In one embodiment, the heating element 14 includes a small amount of iron. The heating element 14 can be made of, for example, a 300 series stainless steel, plated or coated steel, or other magnetically conductive material. In a particular embodiment of the invention, the heating element 14 is made of a 302 series stainless steel.

Both the inductor 12 and the heating element 14 are interventional devices dimensioned to allow implantation inside a body with minimal intrusion. Typically, interventional devices are inserted inside a body through an orifice such as the urethra or the esophagus or, alternatively, through a small incision. In an illustrative embodiment of the invention, the inductor 12 is inserted using a carrier 13, shown in FIG. 1A. Examples of carriers 13 include, but are not limited to: catheter, stent, probe, guide wire, endoscope, needle, and sensor. According to a further illustrative embodiment, the heating element 14 is implanted using a mulit-cannula delivery system, shown in FIG. 4A. According to one feature, the inductor 12 is inserted inside the body through a cavity and the heating element 14 is implanted inside the body proximate to a tissue site to be treated. In a particular embodiment, the inductor 12 is inserted inside the urethra near the prostate and the heating element 14 is implanted inside the prostate to treat benign prostate hyperplasia (BPH). In other embodiments, the inductor 12 is inserted inside the body through other cavities near another organ or tissue to be treated, and the heating element 14 is implanted inside the organ or tissue. The inductor 12 may be disposable or, alternatively, reusable. The heating element 14 may be implanted temporarily or, alternatively, substantially permanently.

In the illustrative embodiment of FIG. 1A, the heating element 14 is depicted as a substantially straight wire having a round outer surface. According to the illustrative embodiment of FIG. 1B, the diameter 15 of the heating element 14 ranges from about 0.005 inches to about 0.032 inches depending, at least in part, upon the desired tissue defect and the size of the treatment site. However, according to the invention, the heating element 14 may be formed in a variety of shapes and sizes without deviating from the scope of the invention.

Figure 1C:
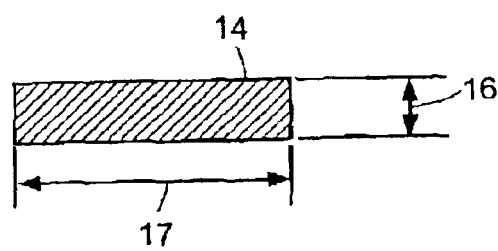

By way of example, in the illustrative embodiment of FIG. 1C, the heating element 14 is formed as a substantially straight wire having at least one substantially flat surface. More particularly, in FIG. 1C, the heating element 14 is formed from a flat wire having a substantially rectangular cross-section. According to one feature, the substantially flat outer surface of the heating element 14 improves its echogenicity to facilitate ultrasonic visualization during implantation of the heating element 14. Preferably, the width 17 of the flat wire ranges from about 0.004 inches to about 0.010 inches with thickness 16 ranging from about 0.001 inches up to about 0.005 inches. However, other dimensions may be employed without deviating from the scope of the invention.

Figure 2A:
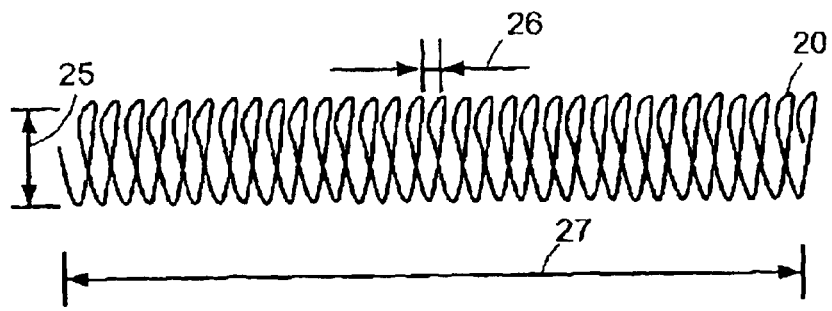
FIGS. 2A–2G show various illustrative heating element configurations, which may be employed with the induction heating apparatus of FIG. 1A.

FIGS. 2A–2G depict various illustrative configurations for the heating element 14, any of which may be employed with the induction heating apparatus 10 of FIG. 1A. Referring to FIG. 2A, in another illustrative embodiment, the heating element 14 is formed as a coil 20. The coil 20 may be open or closed. In one embodiment, the coil diameter 25 ranges from about 0.010 inches to about 0.032 inches, depending, at least in part, upon the magnetic intensity of the wire, desired ultrasound echogenicity, and parameters of the delivery system. In a particular version of this embodiment of the invention, the coil diameter 25 is about 0.014 inches so that the coil 20 fits within a 23TW-gauge needle with inside diameter ranging from about 0.0165 inches to about 0.018 inches. The coil spacing 26 is up to about 0.02 inches depending, at least in part, upon the desired amount of magnetic coupling. In a particular embodiment of the invention, there is substantially no spacing between the coils of the heating element 14. The coil length 27 ranges from about 5 mm to about 100 mm depending upon the size of the tissue defect at the treatment site. According to one illustrative embodiment, the number of coils used ranges up to about 30 depending, for example, upon the size of the tissue defect, the size of the treatment site and the treatment configuration as determined by a physician.

Figure 2B:
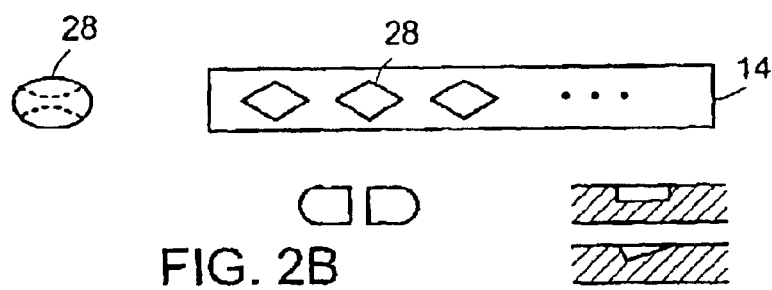
Figure 2C:
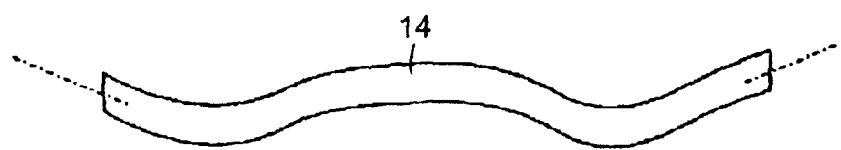
Figure 2D:
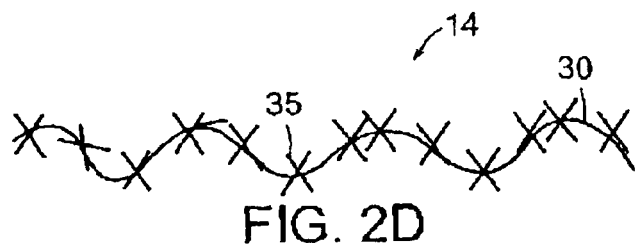
Figure 2E:
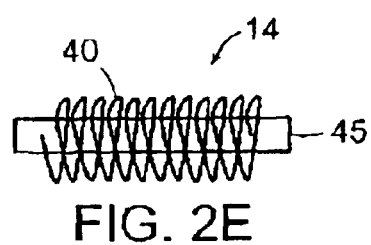
Figure 2F:
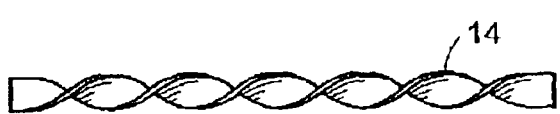
Figure 2G:

The heating element 14 may be formed in other configurations, such as those shown in FIGS. 2B–2G. For example, the heating element 14 may be a roll form wire with embossing or detents 28 on the surface, as shown in FIG. 2B. The heating element 14, as shown in FIG. 2C, may be formed to have a structural resiliency that allows it to be delivered in a substantially straight form and to assume a serpentine form when placed in the body. Materials for achieving such structural resiliency are well known in the art. FIG. 2D depicts a heating element 14 formed as a wire 30 having bristles 35 extending radially therefrom. Referring to FIG. 2E, a heating element 14 comprises a coil 40 with a center core 45 that serves to stiffen the heating element. The core 45 may comprise a radiopaque material to improve the visibility of the heating element 14. In FIGS. 2F and 2G, the heating element 14 is depicted in the shape of a twisted round wire and a twisted flat wire, respectively.

Each of the configurations of the heating element 14 shown in FIGS. 2A–2G provides, as compared to the straight wire of FIGS. 1B and 1C, increased surface area and mass, without increasing the size of the heating element 14. These configurations also improve resistance to migration of the heating element 14 inside a body. In one embodiment, the length of the heating element 14 varies depending upon the application and the size of the treatment site. For example, the heating element 14 may be configured to be shorter where the treatment site is smaller. According to another illustrative feature, the heating element 14 may be cut to an appropriate length prior to use through visual measurement or may be pre-cut to an appropriate size for a specific application.

In some illustrative embodiments, a single heating element is employed. However, other illustrative embodiments employ multiple heating elements. For example, when treating prostate cancer or benign prostate hyperplasia (BPH), a single heating element may be used per lobe. Alternatively, in other configurations, up to three or more heating elements may be used per lobe.

Referring back to FIG. 1A, in operation, a medical operator implants the heating element 14 adjacent a tissue site to be treated, and then inserts the inductor 12 inside the body in close proximity to the heating element 14. The medical operator then applies an alternating current generated by the RF power source 19 to the inductor 12 so that an electromagnetic field is generated between the inductor 12 and the heating element 14 through magnetic coupling. The electromagnetic field induces a current in the heating element 14. The induced current in combination with the electrical resistance of the material of the heating element 14 generates heat. Additionally, magnetic hysteresis, which results from molecular friction caused by magnetizing, demagnetizing, and remagnetizing the heating element 14 in opposite directions by the alternating current, also generates heat. Thus, generated heat ablates tissue adjacent to the heating element 14.

The magnitude and duration of alternating current applied to the inductor 12 can be varied depending on the application and the duty cycle of the apparatus 10. In one illustraitve embodiment, current pulses are applied to the inductor 12. In another illustrative embodiment, a relatively high-amperage current is applied to the inductor 12 for a short period of time to instantaneously heat a tissue site. In an alternative illustrative embodiment, the medical operator slowly heats the tissue by applying a relatively low-amperage current to the inductor 12 to dissipate heat. This embodiment facilitates treatment of a larger tissue site and reduces the risk of charring the tissue surface.

Figure 3A:
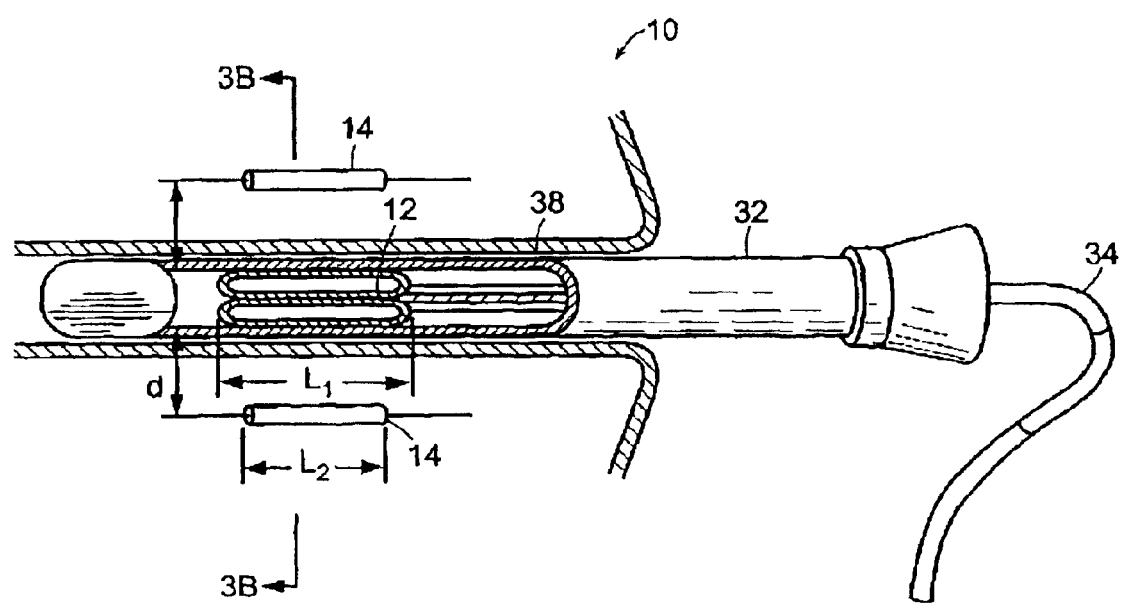
FIG. 3A shows a detailed view of an inductor placed inside a probe of the induction heating apparatus of FIG. 1A inserted into a body cavity, according to an illustrative embodiment of the invention.
Figure 3B:
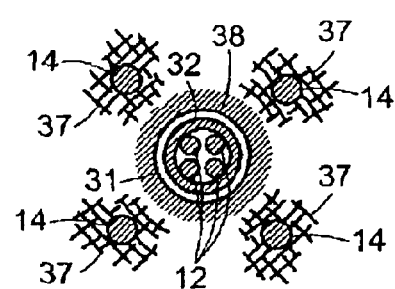
FIG. 3B shows a cross-sectional view of the induction heating apparatus of FIG. 3A taken along the line BB.

Referring to FIGS. 3A and 3B, in another illustrative embodiment of the invention, the inductor 12 is placed in a urethra and the heating elements are implanted in the prostate surrounding the urethra, substantially parallel to the inductor. In this embodiment, the inductor 12 is placed inside a carrier 32. The carrier 32 includes any suitable magnetically transparent material, for example, silicone, latex, or urethane. In a preferred embodiment of the invention, the carrier 32 is a probe having a silicone tube. In an illustrative embodiment of the invention, shown in FIG. 3A, the probe 32 is dimensioned to fit inside a urethra 38. In a preferred embodiment, the probe 32 is about 430 mm long, has an outer diameter of about 7.3 mm and an inner diameter of about 5.0 mm. In the alternative illustrative embodiment of the invention, instead of the probe 32, the medical operator uses a Foley catheter (not shown) to deliver the inductor 12.

Referring still to FIG. 3A, in an illustrative embodiment, the inductor 12 includes a RF coil portion having two loops.

In one embodiment, the coil portion of the inductor 12 has a length $L_1$ of about 5 cm and an outside diameter of about 5 mm. Other lengths of the RF coil portion may be employed without deviating from the scope of the invention. The induction heating apparatus 10 further includes a plurality of heating elements 14, which are positioned near and substantially parallel to the coil portion of the inductor 12. For example, in one embodiment, each heating element 14 has a length $L_2$ ranging from about 2 cm to 5 cm and a diameter of about 1 mm. Other shapes and dimensions of the heating element 14 can be employed without deviating from the scope of the invention. According to one feature of this embodiment, the distance d between the inductor 12 and each heating element 14 is about 1 cm. Alternatively, the distance d can be longer or shorter, depending on the position and the size of the tissue site to be treated. A RF cable 34 electrically couples the inductor 12 with an RF power source (not shown).

FIG. 3B shows a cross-sectional view of the induction heating apparatus 10 of FIG. 3A taken along the line BB. The electromagnetic field 31 is generated by the inductor 12. The tissue area 37 around each heating element 14 is treated through induction heating induced by the electromagnetic field 31.

Figure 4A:
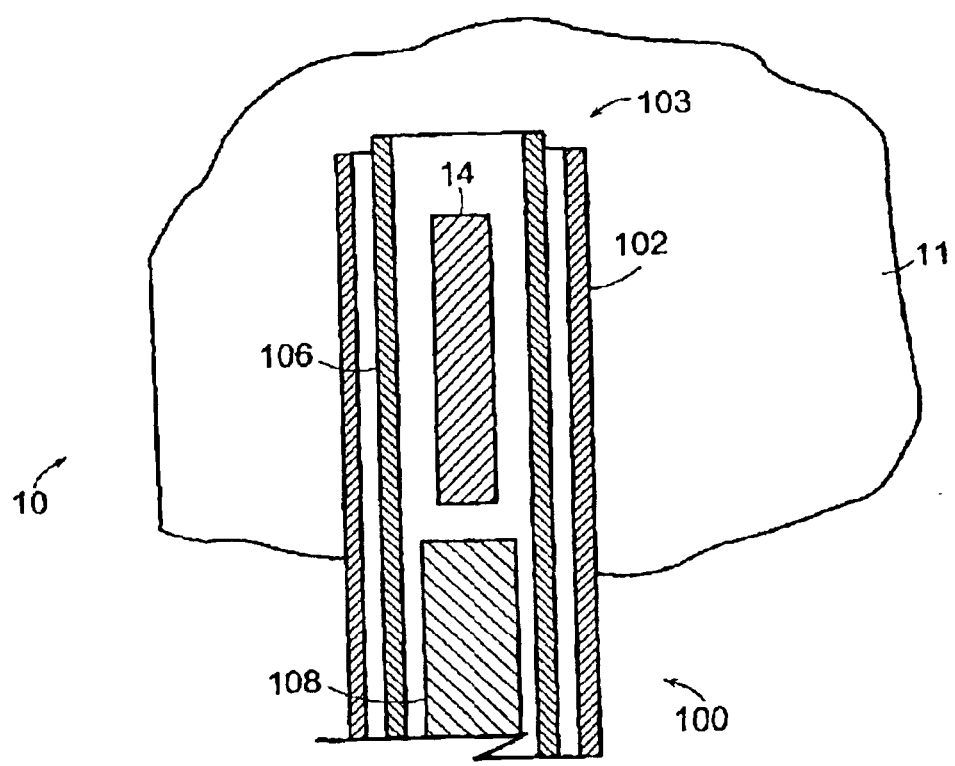
FIG. 4A depicts a heating element, which may be employed with the induction heating apparatus of FIG. 1A, inserted into a body tissue using a multi-cannula delivery system, according to an illustrative embodiment of the invention.

Referring to FIG. 4A, the illustrative induction heating apparatus 10 of the invention further includes a multi-cannula delivery system 100 for delivering the heating element 14 to the tissue site 11. In an illustrative embodiment, the multi-cannula delivery system 100 includes an outer cannula 102, an inner cannula 106, and an inner stylet 108. According to one feature, the heating element 14 can be preloaded into the inner cannula 106 prior to insertion of the inner cannula 106 into the desired tissue site 11. According to another feature, the heating element 14 may be loaded in the inner cannula 106 subsequent to inserting the inner cannula 106 into the body.

Figure 4B:
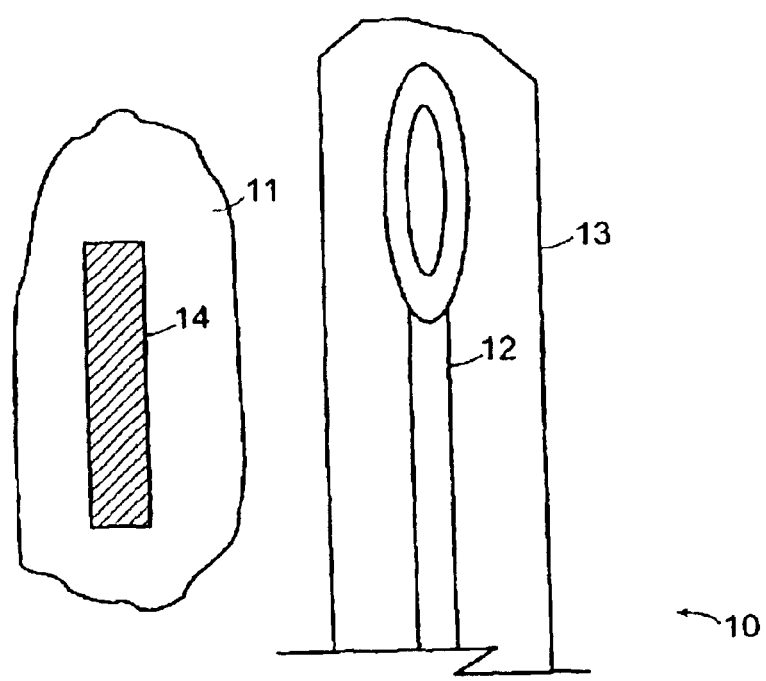
FIG. 4B shows an inductor and a heating element, which may be employed with the induction heating apparatus of FIG. 1A, inserted inside a body.

Still referring to FIG. 4A, in operation, the heating element 14 is discharged from the inner cannula 106 and implanted into the body tissue site 11. Subsequent to inserting the heating element 14 into the inner cannula 106, a medical operator positions the inner stylet 108 in the inner cannula 106 to maintain the position of the heating element 14 when the outer cannula 102 and the inner cannula 106 are withdrawn over the inner stylet 108. After the heating element 14 is implanted, the medical operator removes the outer cannula 102, the inner cannula 106, and the inner stylet 108 from the body. In an illustrative embodiment, the medical operator implants the heating element 14 into the body tissue site 11 under ultrasound visualization. In this embodiment, at least a portion of the multi-cannula delivery system 100 is formed to be substantially echogenic, for example, by creating a textured or rough surface, or by including bubbles or fluid therein. According to one feature, a distal end 103 of the outer cannula 102 is formed to be substantially echogenic. As shown in FIG. 4B, in an illustrative embodiment of the invention, subsequent to implanting the heating element 14, the medical operator introduces the inductor 12 in close proximity to the heating element 14.

Figure 5A:
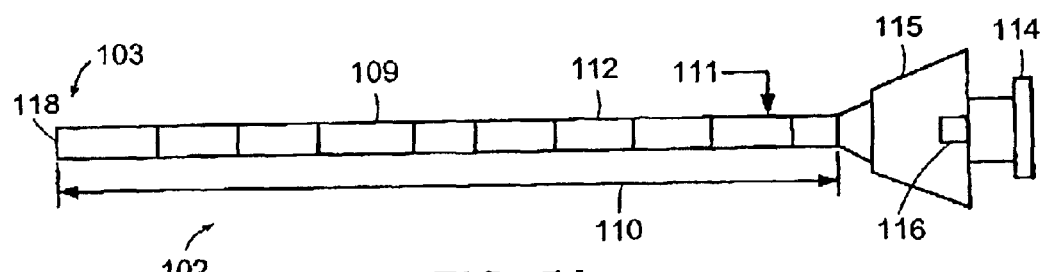
FIG. 5A shows an outer cannula, which may be employed with the multi-cannula delivery system of FIG. 4A.
Figure 5B:
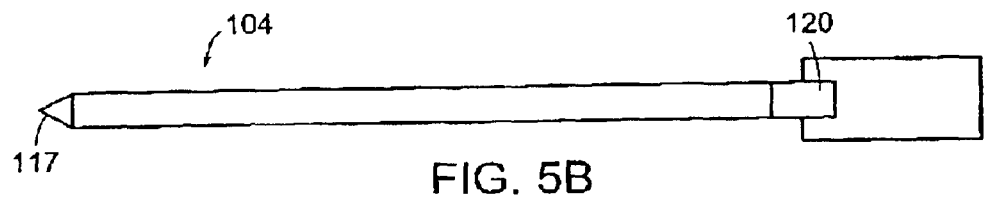
FIG. 5B shows an outer stylet of the multi-cannula delivery system of FIG. 4A, adapted for insertion into the outer cannula of FIG. 5A.

FIGS. 5A–5D depict various illustrative components of the multi-cannula delivery system 100. Referring to FIG. 5A, the system 100 includes an outer cannula 102. In one illustrative embodiment, the outer cannula 102 has an 18-gauge standard-wall hypodermic tube 109. In an alternative illustrative embodiment, the outer cannula 102 has a 19-gauge thin-wall hypodermic tube 109. In one illustrative embodiment, the length 110 of the tube 109 ranges from about 7 to about 10 inches. In a particular embodiment of the invention, the tube 109 is about 8 inches long. Optionally, the outer cannula 102 also has a lubricious coating on the outer surface 111 to reduce friction during insertion to the patient's body. Also, optionally, the outer cannula 102 includes distance markings 112 thereon to facilitate visual control over accuracy of placement during the insertion. Referring to FIGS. 5A and 5B, in one illustrative embodiment, the outer cannula 102 further includes a female luer fitting 114 on a hub 115 and a notch 116, for receiving a hub key 120 of the outer stylet 104. In some embodiments, at least a portion of the outer cannula 102 is substantially echogenic. By way of example, the outer cannula 102 may have an echogenic distal tip 103 to facilitate ultrasound visualization.

Referring to FIG. 5B, in one illustrative embodiment, the system 100 also includes the outer stylet 104 adapted to fit inside the outer cannula 102. In one illustrative embodiment, the outer stylet 104 has a distal cutting tip 117, such as a trocar or a tapered tip. According to one feature, the outer stylet 104 has the hub key 120 to mate with the notch 116 of the outer cannula 102, thereby enabling locking of the outer stylet 104 to the outer cannula 102.

Figure 5C:
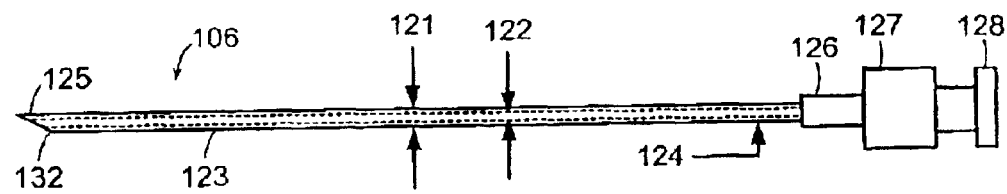
FIG. 5C shows an inner cannula of the multi-cannula delivery system of FIG. 4A, adapted for insertion into the outer cannula of FIG. 5A.

Referring to FIG. 5C, as described above with respect to FIG. 4A, the system 100 includes the inner cannula 106 adapted to fit inside the outer cannula 102 when the outer stylet 104 is removed therefrom. The outer diameter 121 of the inner cannula 106 is sufficiently small so that the inner cannula 106 may fit smoothly inside the outer cannula 102. In some embodiments, the inner cannula 106 has an inside diameter 122 sized to receive the heating element 14 therein. In a particular embodiment, the inner cannula 106 includes a 22-gauge standard-wall hypodermic tube 123 having a substantially smooth inner surface 124. Optionally, the distal tip 125 of the inner cannula 106 is a bevel tip.

As shown in FIGS. 5A and 5C, according to an illustrative embodiment of the invention, the inner cannula 106 has a male luer fitting 126 on a hub 127 adapted to mate with the female luer fitting 114 on the hub 115 of the outer cannula 102. According to a further embodiment, the inner cannula 106 also has a female luer fitting 128 adapted to mate with the male luer 134 of the inner stylet 108, shown in FIG. 5D.

Figure 5D:
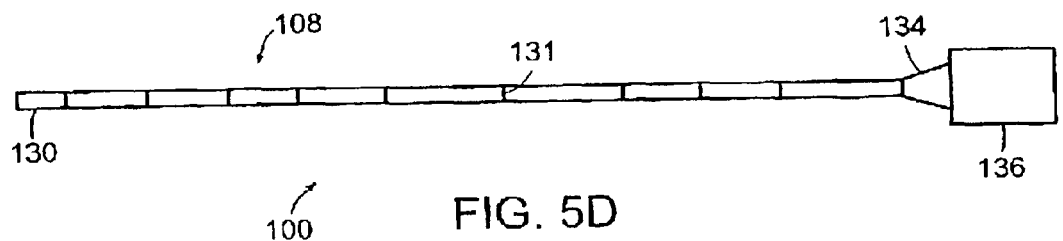
FIG. 5D shows an inner stylet of the multi-cannula delivery system of FIG. 4A, adapted for insertion into the inner cannula of FIG. 5C.

Referring to FIG. 5D, in the illustrative embodiment of the invention, the system 100 further includes the inner stylet 108 adapted to fit inside the inner cannula 106. According to one feature, the inner stylet 108 has a blunt distal tip 130. Optionally, the inner stylet 108 has distance markings 131 thereon. The inner stylet 108 may also have a male luer fitting 134 on a hub 136 to mate with the female luer fitting 128 of the inner cannula 106.

Figure 6A:
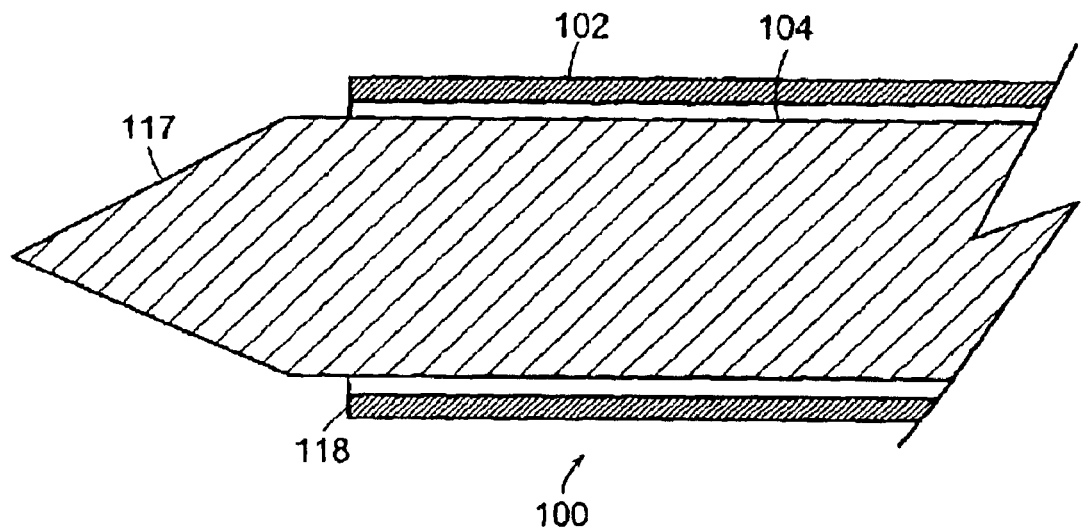
FIG. 6A is a cross-sectional view of the distal end of the multi-cannula delivery system of FIG. 4A taken along a longitudinal axis and depicting the outer stylet of FIG. 5B inserted into the outer cannula of FIG. 5A, according to an illustrative embodiment of the invention.

FIG. 6A depicts a portion of the outer stylet 104 of FIG. 5B inserted into the outer cannula 102 of FIG. 5A according to an illustrative embodiment of the invention. Referring to FIG. 6A, in operation, a medical operator places the outer stylet 104 into the outer cannula 102 and then inserts the outer cannula 102 with the outer stylet 104 locked therein into the desired treatment site. The outer stylet 104 is preferably longer than the outer cannula 102, so that the distal end 117 of the outer stylet 104 protrudes beyond the distal opening 118 of the outer cannula 102. Subsequent to inserting the outer cannula 102, with the outer stylet 104 locked therein, into the desired treatment site, the medical operator removes the outer stylet 104 from the outer cannula 102.

Figure 6B:
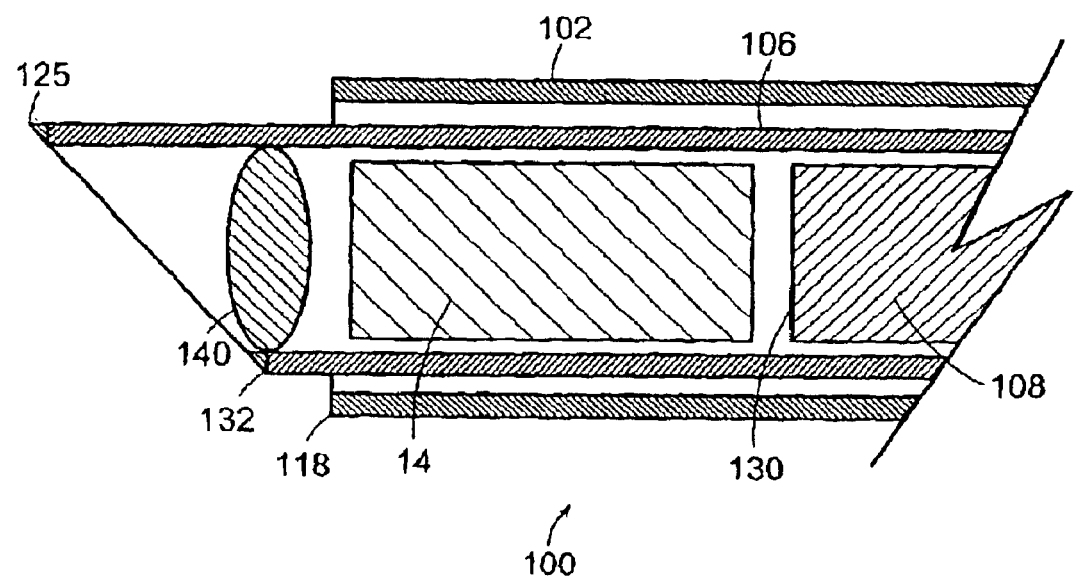
FIG. 6B is a cross-sectional view of the distal end of the multi-cannula delivery system of FIG. 4A taken along a longitudinal axis and depicting the inner cannula of FIG. 4C having an illustrative heating element of FIGS. 2A–2G and the inner stylet of FIG. 5D placed therein and inserted into the outer cannula of FIG. 5A, according to an illustrative embodiment of the invention.

FIG. 6B depicts the inner cannula 106 of FIG. 5C having an illustrative heating element of the type depicted in FIGS. 1B–2G and the inner stylet of FIG. 5D placed therein inserted in the outer cannula of FIG. 5A, according to an illustrative embodiment of the invention. Referring to FIG. 6B, in some embodiments, a medical operator loads the heating element 14 inside the inner cannula 106 in advance of the insertion inside the body, so that the inner cannula 106 having the heating element 14 therein is stored prior to the procedure. In other embodiments, the medical operator loads the heating element 14 into the inner cannula 106 immediately prior to implantation. According to one feature, the heating element 14 is loaded when the inner cannula 106 is substantially within the patient's body. In some embodiments, the heating element 14, cut to a desired length, is loaded inside the inner cannula 106 using a pair of tweezers. In other embodiments, the heating element 14, cut to a desired length, can be loaded inside the inner cannula 106 using a multi-cannula delivery system loading device, an illustrative embodiment of which is shown in FIG. 6.

As shown in the illustrative embodiment of FIG. 6B, the length of the inner cannula 106 is sufficient to allow the distal tip 125 to protrude slightly past the distal opening 118 of the outer cannula 102 when the inner cannula 106 is coupled to the outer cannula 102. Optionally, the distal tip 125 of the inner cannula 106 can be plugged with a bone wax 140. According to one feature, the inner stylet 108 is dimensioned so that its distal tip 130 protrudes past a proximal edge 132 of the distal tip 125 of the inner cannula 106.

Referring back to FIG. 6A, as mentioned above, in operation, the medical operator assembles the outer cannula 102 and the outer stylet 104, and then transperinealy inserts the assembly into the patient's body under ultrasound visualization proximal to a tissue region to be treated, such as the prostate. During implantation, the cutting tip 117 of the outer stylet 104 penetrates tissue. After desired placement inside the body, the outer stylet 104 is unlocked and removed from the outer cannula 102 and the patient's body.

According to the illustrative embodiment of FIG. 6B, subsequent to withdrawal of the outer stylet 104, the medical operator inserts the inner cannula 106 having the heating element 14 and the inner stylet 108 therein into the outer cannula 102. The inner stylet 108 is placed inside the inner cannula 106 so that it is in contact with the heating element 14.

Still referring to FIG. 6B, according to one feature of the invention, the medical operator then pushes the heating element 14 towards the distal tip 125 of the inner cannula 106 using the inner stylet 108 until the heating element 14 begins to push out the bone wax 140. Then, the medical operator typically applies pressure to the inner stylet 108 to hold the heating element 14 in place while he or she withdraws the inner cannula 106 and the outer cannula 102 from the treatment site over the inner stylet 108 to expose the heating element 14, as observed by the ultrasound equipment. The illustrative implantation process concludes with a removal of the inner stylet 108 from the patient's body.

As depicted in FIGS. 7A–7E, the multi-cannula delivery system 100 employ a variety of inner cannula 106 configurations without deviating from the scope of the invention. By way of example, the inner cannula 106 of FIGS. 7A and 7B has a trocar point 208 and an eccentric bore 210 at the distal tip 125. The bore 210 has an opening 211 on one face 212 of the trocar point 208. According to one feature, the trocar point 208 improves tissue penetration during insertion. More specifically, when inserted into a tissue, for example, a prostate, the inner cannula 106 of this embodiment of the invention is less likely to splay as compared to an inner cannula having, for example, a bevel tip.

According to the illustrative embodiment of FIG. 7C, the inner cannula 106 has a Huber point 213 at the distal tip 125. The Huber point 213 is formed by bending the tip of the inner cannula 106 so that the opening 214 of the bore 216 appears to be through the side of the cannula 106. Because the opening 214 is provided only on a side of the cannula 106, the Huber point 213 improves insertion by reducing tissue penetration into the bore 216. In this embodiment, the penetrating Huber point 213 falls on the central axis 215 of the inner cannula 106 to reduce splaying when the inner cannula 106 is placed inside tissue. According to one feature of the invention, because of its flexibility, the heating element 14 (not shown) exits the bore 216 through the opening 214.

Figure 7D:
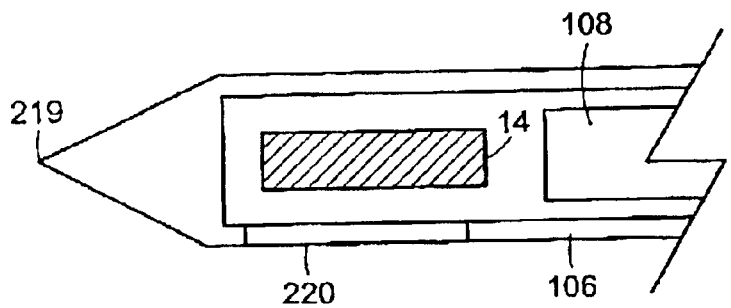
FIG. 7D shows a cross-sectional side view taken along a longitudinal axis of an inner cannula of the illustrative multi-cannula delivery system of FIG. 4A having a trocar point and a side opening at its distal end, according to a further illustrative embodiment of the invention.

According to the illustrative embodiment shown in FIG. 7D, the inner cannula 106 has a trocar point 219 and a side opening 220 in the side wall of the inner cannula 106. In this embodiment, the trocar point 219 is solid, which generally facilitates tissue penetration. In operation, the heating element 14 is released through the side opening 220 using the inner stylet 108.

Figure 7E:
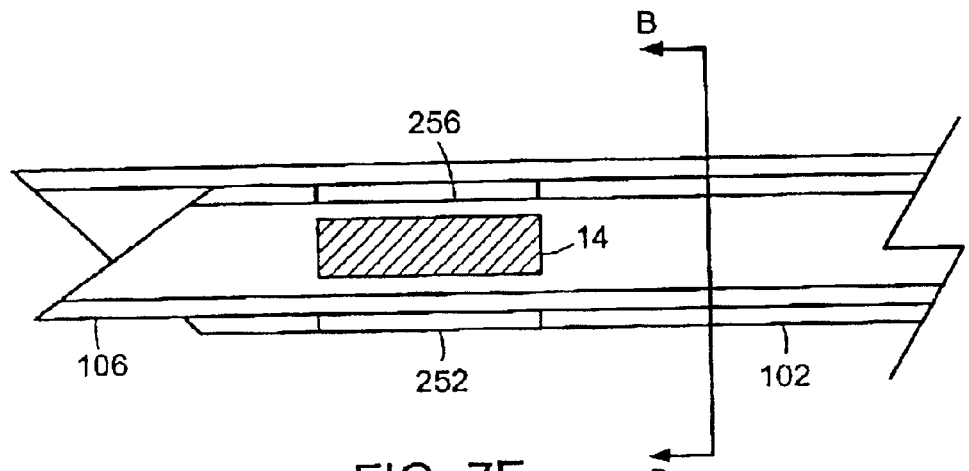
FIG. 7E shows a cross-sectional side view taken along a longitudinal axis of an outer cannula and an inner cannula of the multi-cannula delivery system of FIG. 4A each having side openings at their respective distal ends according to an additional illustrative embodiment of the invention.
Figure 7F:
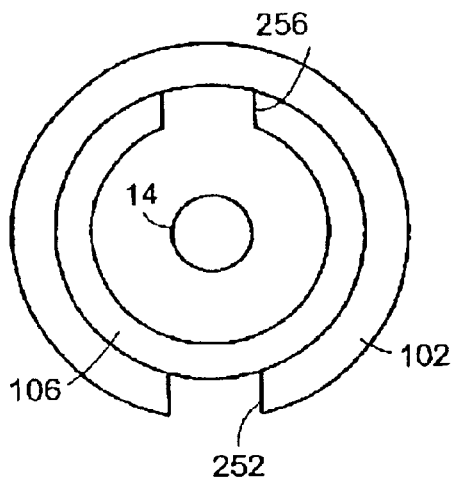
FIG. 7F shows a cross-sectional view taken along the line BB of the inner cannula and the outer cannula of FIG. 7E in a closed position.
Figure 7G:
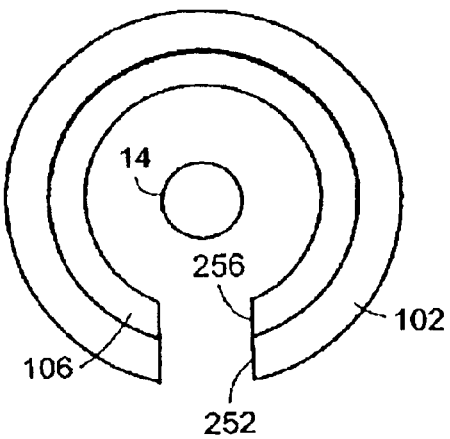
FIG. 7G shows a cross-sectional view taken along the line BB of the inner cannula and the outer cannula of FIG. 7E in an open position.

According to the illustrative embodiment shown in FIGS. 7E–7G, the outer cannula 102 and the inner cannula 106 have longitudinal openings 252 and 256 respectively at their respective distal ends. The openings 252, and 256 are located in side walls of the outer cannula 102 and the inner cannula 106 proximal to the distal ends thereof. The inner cannula 106 is generally capable of rotation relative to the outer cannula 102 so as to cause the longitudinal openings to substantially align. According to one feature of the invention, the openings 252 and 256 are dimensioned to control release of the heating element 14 in a desired orientation. When the opening 252 of the outer cannula 102 and the opening 256 of the inner cannula 106 are substantially aligned as shown in FIG. 7G, the heating element 14 inside the inner cannula 106 is released. After the heating element 14 is released through the openings 252 and 256, as observed by the ultrasound equipment, the outer cannula 102, the inner cannula 106, and the inner stylet 108 are removed from the body.

As shown in FIG. 7E, in one illustrative embodiment of the invention, the outer cannula 102 and the inner cannula 106 each has a 45-degree bevel cutting tip at their respective distal ends. When the outer cannula 102 and the inner cannula 106 loaded with the heating element 14 are inserted inside the body, the openings 252 and 256 are placed opposite each other (see FIG. 7F) and a substantially closed tube with a conical cutting tip is formed. When the medical operator rotates the outer cannula 102 and the inner cannula 106 relative to one another to align the openings 252 and 256, the distal tip of the inner cannula 106 rests inside the tip of the outer cannula 102.

The heating element can be loaded into a multi-cannula delivery system in a variety of ways. According to the illustrative embodiment of FIG. 8, the heating element 14 in a shape of a coil 72 is loaded in the following manner. A round container 74 containing the coil 72 therein is attached to a base 71 of a multi-cannula delivery system loading device 70 shown in FIG. 8. In other embodiments, various wire cassettes such as a spool, a cartridge and a feed screw shown in FIGS. 9A–9D can be attached to the base 71 of the multi-cannula delivery system loading device 70 to replace the container 74.

In operation, a medical operator feeds a loose end of the coil 72 through a lead hole 76 into a groove 78 formed in the base 71. Using a pair of tweezers or other suitable mechanism, the medical operator grasps the end of the coil 72 and pulls it out to a desired length. In one embodiment, the length of the coil 72 is measured using a cutoff scale 79. Using a pair of scissors or other suitable mechanism, the medical operator cuts the coil 72 at the location of the cutting slot 80. The coil 72 is released and dropped through a loading slot (not shown) into a discharge tube 86 axially disposed in the groove 78. Then, the medical operator inserts a female luer port of the multi-cannula delivery system (not shown) into a male luer port 84 at the end of the discharge tube 86. By applying pressure to the coil 72, the medical operator transfers the coil 72 from the discharge tube 86 into the multi-cannula delivery system 100 through the luer port 84. Then, the multi-cannula delivery system 100, with the loaded heating element, is removed from the loading device 70. In one illustrative embodiment of the invention, the medical operator applies pressure to the coil 72 in the discharge tube 86 using an actuator, for example, a plunger 88 shown in FIG. 6. Other pressurizing mechanisms known in the art may be employed instead of the plunger 88 without deviating from the scope of the invention.

Figure 10:
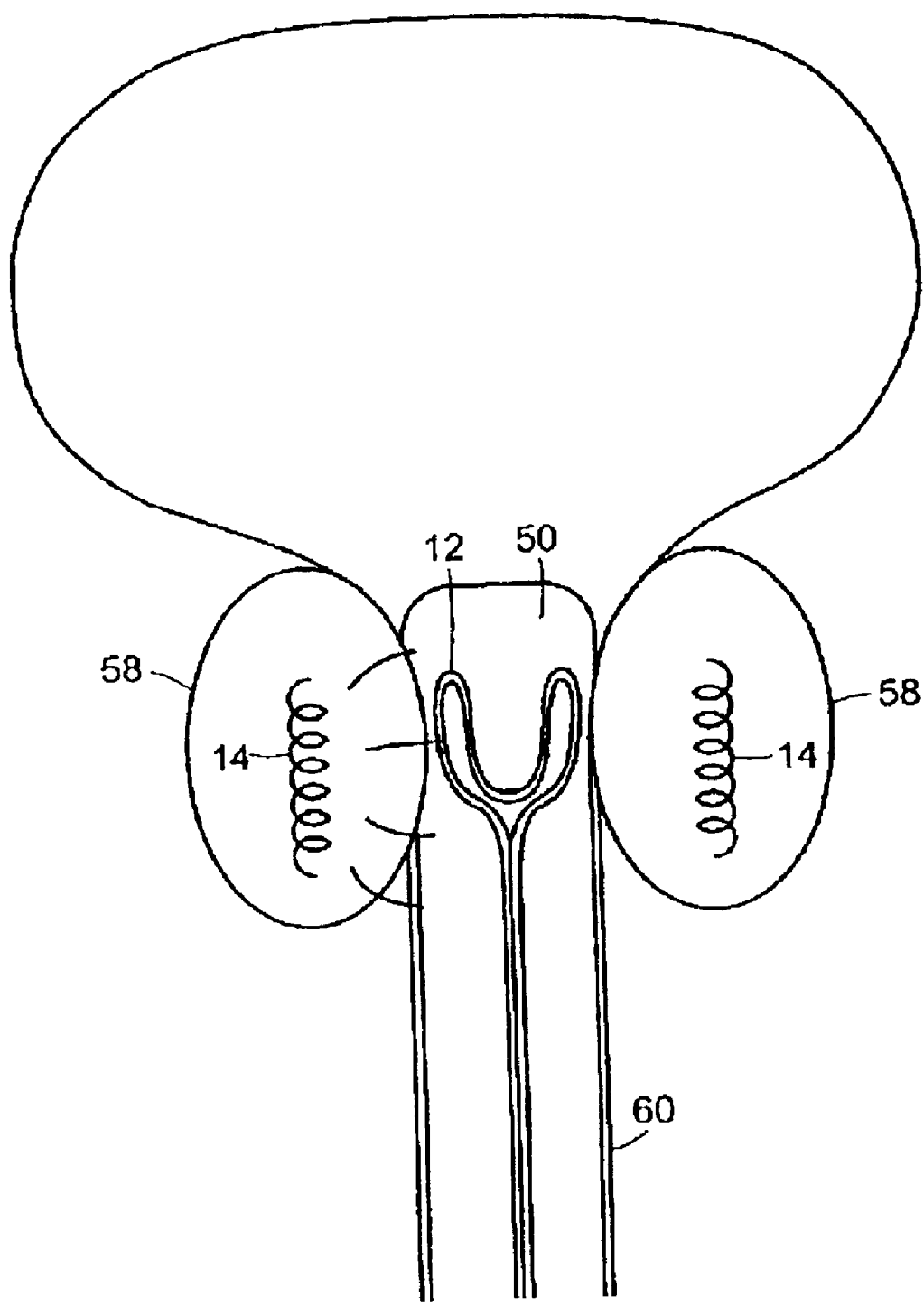
FIG. 10 shows an inductor and a heating element of an induction heating apparatus inserted into a body for treating BPH, according to an illustrative embodiment of the invention.

Referring to FIG. 10, in one illustrative embodiment, the induction heating apparatus of the invention is used for treating BPH. In operation, the medical operator implants the heating element 14 into the prostate 58 through the urethra 60. Prior to implantation of the heating element 14, the medical operator applies local anesthesia to the urethra 60 where a delivery needle (not shown) is intended to puncture the urethra 60 in its passage to the prostate 58. In one version of this embodiment, the delivery needle is placed in the desired location through a resectoscope and advanced to the desired depth in the prostate 58. Additional heating elements 14 can be inserted in the prostate using the same method. Once all the heating elements have been positioned the resectoscope may also be removed. In another version of this embodiment, the heating elements 14 can be implanted inside the prostate transperineally or retropubically using the multi-cannula delivery system 100 (not shown) described above in connection with FIGS. 4A–6B. In this embodiment, an incision is made near the rectum and the heating element 14 is inserted substantially parallel to the rectum.

During treatment, the medical operator inserts a carrier 50, such as, for example, a catheter or a probe, containing the inductor 12 inside the urethra 60 through a resectoscope, as shown in FIG. 10, and an alternating current is applied to the inductor 12 thereby causing the heating elements 14 to generate heat in the treatment site in the prostate 60. When the procedure is completed, the medical operator removes the carrier 50 containing the inductor 12. The heating element 14, however, may remain in the body for future treatments, if necessary. An advantage of this treatment over interstitial RF ablation is that since the heating element 14 and the inductor 12 are not in physical contact, a risk of damage to the urethral wall is reduced.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An induction heating apparatus, comprising:
 a first interventional device comprising an electrically conductive material, said first interventional device adapted for implantation inside a body at a first implantation location and for receiving an alternating current; and
 a second interventional device comprising a magnetically conductive material, said second interventional device adapted for implantation inside the body at a second implantation location in close proximity to said first interventional device and for magnetically coupling with said first interventional device to generate heat upon application of said alternating current to said first interventional device.

2. The apparatus of claim 1 wherein said first interventional device comprises an inductor.

3. The apparatus of claim 2 wherein said first interventional device comprises a radio-frequency coil.

4. The apparatus of claim 2 wherein said first interventional device further comprises a carrier.

5. The apparatus of claim 4 wherein said carrier is selected from the group consisting of: catheter, stent, probe, guide wire, endoscope, needle, and sensor.

6. The apparatus of claim 1 wherein said second interventional device comprises at least one of the group consisting of a substantially straight round wire, a substantially straight flat wire, a detented wire, an embossed wire, a bristled wire, a shaped resilient wire, a twisted round wire, a twisted flat wire, and a coil with an inner core.

7. The apparatus of claim 1 wherein said second interventional device comprises a coil.

8. The apparatus of claim 7 wherein said coil has a variable length.

9. The apparatus of claim 7 wherein said second interventional device comprises a magnet coil.

10. The apparatus of claim 1 further comprising a power source, in electrical communication with said first interventional device, and adapted to provide power to said first interventional device.

11. The apparatus of claim 10 further comprising a controller, in electrical communication with said power source, and adapted to control power to said first interventional device.

12. The apparatus of claim 1 further comprising a multi-cannula delivery system for implantation of said second interventional device inside said body.

13. The apparatus of claim 12 wherein said multi-cannula delivery system comprises an outer cannula and an inner cannula; said inner cannula having a distal tip and an outer diameter sufficiently small to fit inside said outer cannula.

14. The apparatus of claim 13 wherein said inner cannula has an inner diameter sufficiently large to receive said second interventional device therein.

15. The apparatus of claim 13 further comprising an outer stylet having a distal tip and an outer diameter sufficiently small to fit inside said outer cannula.

16. The apparatus of claim 13 further comprising an inner stylet having a distal tip and an outer diameter sufficiently small to fit inside said inner cannula.

17. The apparatus of claim 13 wherein said distal tip of said inner cannula is plugged.

18. The apparatus of claim 13 wherein said distal tip of said inner cannula comprises a trocar.

19. The apparatus of claim 18 wherein said inner cannula has a side opening proximal to said distal tip.

20. The apparatus of claim 13 wherein said outer cannula and said inner cannula comprise longitudinal openings.

21. The apparatus of claim 20 wherein said inner cannula is adapted to be capable of rotating in relation to said outer cannula so as to cause said longitudinal openings to align.

22. The apparatus of claim 21 wherein said second interventional device is releasable from said multi-cannula delivery system upon alignment of said longitudinal openings.

23. The apparatus of claim 12 further including a multi-cannula delivery system loading device, comprising:
a base,
a container attached to said base and adapted for dispensing said second interventional device therefrom, and
a discharge tube attached to said base and adapted for receiving said second interventional device dispensed from said container and for loading said second interventional device into said multi-cannula delivery system.

24. The apparatus of claim 23 wherein said base defines a groove longitudinally formed therein.

25. The apparatus of claim 24 wherein said second interventional device is dispensed from said container into said groove.

26. The apparatus of claim 25 wherein said discharge tube is disposed in said groove.

27. The apparatus of claim 26 wherein said discharge tube comprises a drop-in slot for receiving said second interventional device therein.

28. The apparatus of claim 23 wherein said container is removably and reusably attached to said base.

29. The apparatus of claim 23 wherein said discharge tube is removably and reusably attached to said base.

30. The apparatus of claim 23 wherein said discharge tube comprises an actuator and a luer port, said actuator and said luer port adapted for loading said second interventional device into said multi-cannula delivery system.

* * * * *